United States Patent [19]

Tsou et al.

[11] Patent Number: 5,135,547
[45] Date of Patent: Aug. 4, 1992

[54] FACILITATED LIQUID MEMBRANES FOR OLEFIN/PARAFFIN GAS SEPARATIONS AND RELATED PROCESS

[75] Inventors: Dean T. Tsou, Solon; Marc W. Blachman, Highland Heights, both of Ohio

[73] Assignee: The Standard Oil Company, Cleveland, Ohio

[21] Appl. No.: 721,909

[22] Filed: Jun. 20, 1991

Related U.S. Application Data

[63] Continuation of Ser. No. 528,849, May 25, 1990, abandoned.

[51] Int. Cl.$^5$ .................... B01D 33/22; B01D 71/68
[52] U.S. Cl. ........................................ 55/16; 55/158; 585/819
[58] Field of Search .................... 55/16, 68, 158; 585/818, 819

[56] References Cited

U.S. PATENT DOCUMENTS

| | | | |
|---|---|---|---|
| 3,335,545 | 8/1967 | Robb et al. | 55/16 |
| 3,396,510 | 8/1968 | Ward, III et al. | 55/16 |
| 3,410,794 | 11/1968 | Li | 55/16 X |
| 3,447,286 | 6/1969 | Dounoucos | 55/16 |
| 3,503,186 | 3/1970 | Ward, III | 55/16 |
| 3,604,246 | 9/1971 | Toren | 55/16 X |
| 3,624,983 | 12/1971 | Ward, III | 55/16 |
| 3,625,734 | 12/1971 | Ward, III | 55/158 X |
| 3,676,220 | 7/1972 | Ward, III | 55/158 X |
| 3,758,603 | 9/1973 | Steigelmann et al. | 55/16 |
| 3,758,605 | 9/1973 | Hughes et al. | 55/16 |
| 3,770,842 | 11/1973 | Steigelmann et al. | 55/16 X |
| 3,800,506 | 4/1974 | Hughes et al. | 55/16 |
| 3,812,651 | 5/1974 | Steigelmann | 55/16 |
| 3,819,806 | 6/1974 | Ward, III et al. | 55/16 X |
| 3,823,529 | 7/1974 | Hughes et al. | 55/16 |
| 3,844,735 | 10/1974 | Steigelmann et al. | 55/16 |
| 3,864,418 | 2/1975 | Hughes et al. | 55/16 X |
| 3,865,890 | 2/1975 | Steigelmann et al. | 55/16 |
| 3,951,621 | 4/1976 | Hughes et al. | 55/16 |
| 3,980,605 | 9/1976 | Steigelmann et al. | 55/16 X |
| 4,014,665 | 3/1977 | Steigelmann | 55/16 |
| 4,015,955 | 4/1977 | Steigelmann et al. | 55/16 |
| 4,106,920 | 8/1978 | Hughes et al. | 55/16 X |
| 4,230,463 | 10/1980 | Henis et al. | 55/16 |
| 4,235,983 | 11/1980 | Steigelmann et al. | 55/16 X |
| 4,239,506 | 12/1980 | Steigelmann et al. | 55/16 |
| 4,617,029 | 10/1986 | Pez et al. | 55/16 |
| 4,705,544 | 11/1987 | Okita et al. | 55/158 |
| 4,710,205 | 12/1987 | Deetz et al. | 55/16 X |
| 4,737,166 | 4/1988 | Matson et al. | 55/16 |
| 4,761,164 | 8/1988 | Pez et al. | 55/16 |
| 4,762,535 | 8/1988 | Pez et al. | 55/16 |
| 4,780,114 | 10/1988 | Quinn et al. | 55/16 |
| 4,814,443 | 4/1989 | Matson et al. | 55/16 |
| 4,954,145 | 9/1990 | Thakore et al. | 55/158 X |
| 4,961,758 | 10/1990 | Dobitz | 55/16 |

FOREIGN PATENT DOCUMENTS 60-090005  5/1985  Japan .................... 55/158

OTHER PUBLICATIONS

LeBlanc, Jr. et al. *J of Memb. Sci.*, 6 (1980) 339–343, "Facilitated Transport in Ion-Exchange Membranes".
Hosseiny et al., *Inorganica Chimica Acta*, 49 (1981) 99–105, "The Coordination Chemistry of Manganese, Part VII, The Preparation and Spectroscopic Characterisation of some Manganese (II) Complexes of Triphenylphosphine of Unusual Stoicheiometry, $Mn(PPH_3)X_2$".
Gott et al., *J. Chem. Soc. Dalton Trans.* 1987, 2241–2243, "The Coordination of Small Molecules by Manganese(II), Phosphine Complexes, Part 9[1], The Reaction of Ethylene with $[MnX_2L](X=Cl, Br, or I; L=PPr^n_3, PBu^n_3, PPhMe_2, PPhEt_2, PPhEt_2, or PPh_3)$ in Tetrahydrofuran Solution".

*Primary Examiner*—Robert Spitzer
*Attorney, Agent, or Firm*—Larry W. Evans; Joseph G. Curatolo; Sue E. Phillips

[57] ABSTRACT

A facilitated liquid membrane for the separation of olefins from a gaseous feed stream comprises a porous support structure (10, 15) and a liquid membrane which comprises an aqueous solution containing a metal salt facilitator capable of coordinating with olefin gases, and an alkyl carbonate co-solvent. A process for the separation of olefins from gaseous feed streams comprises the steps of passing a gaseous feed stream over one side of a facilitated liquid membrane according to the present invention and collecting the olefins on the other side of the membrane.

18 Claims, 5 Drawing Sheets

POLYSULFONE HOLLOW FIBER WATER CELL

POLYSULFONE HOLLOW FIBER ETHYLENE CARBONATE / WATER CELL

ETHYLENE PERMEABILITY IN SPECTRA POR, 2.0 N AgNO$_3$

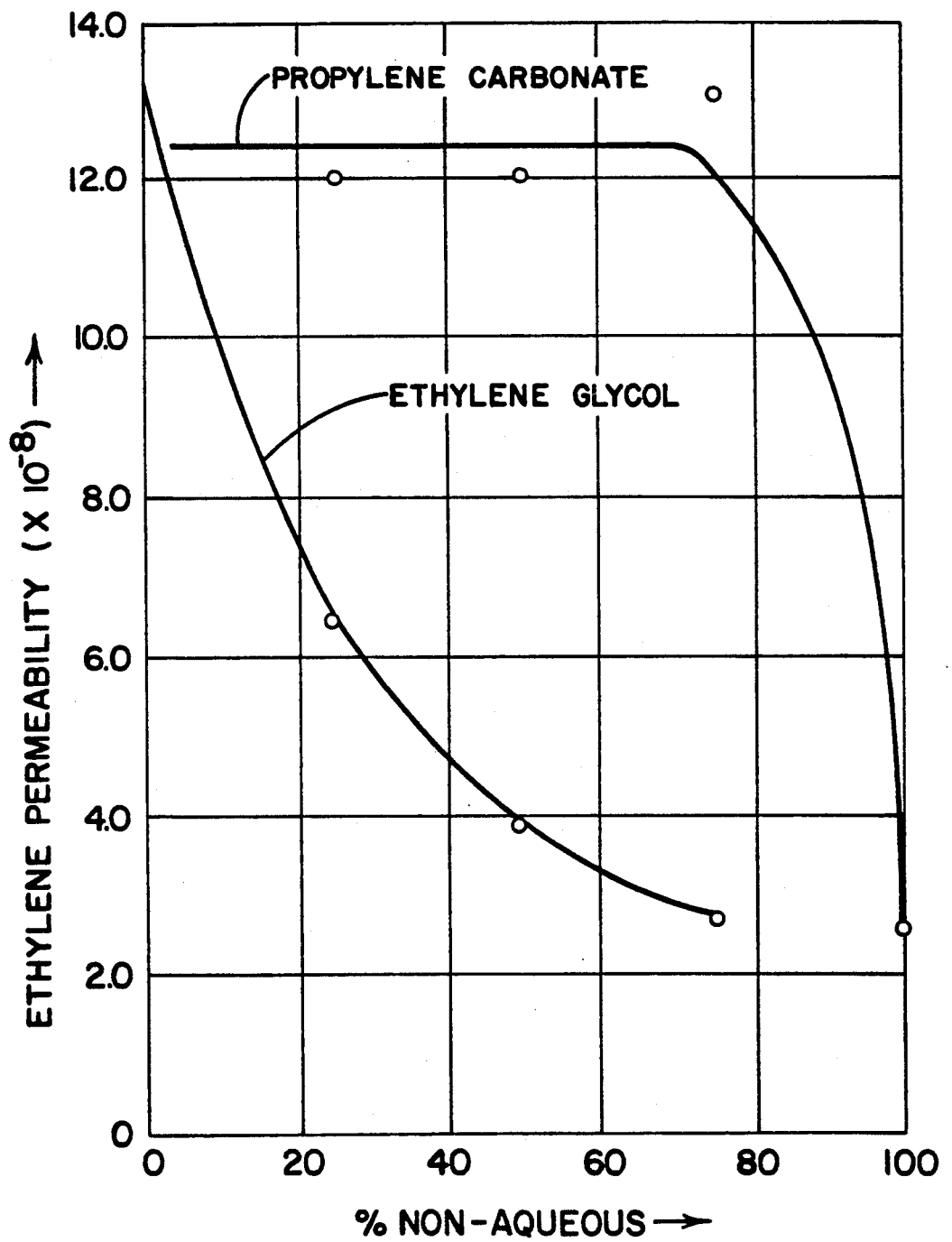

FACILITATED LIQUID MEMBRANES FOR OLEFIN/PARAFFIN GAS SEPARATIONS AND RELATED PROCESS

This application is a continuation of U.S. Ser. No. 528,849, filed May 25, 1990, now abandoned.

TECHNICAL FIELD

The subject invention relates to facilitated liquid membranes and their use for the selective separation of gas stream components. More specifically, the invention relates to the use of alkyl carbonate liquids carried by a porous support member for olefin gas separations. The invention also provides a process for the selective separation of at least one gas from a feed stream. Such a process can be used in manufacturing or reclamation where the separation of olefins from other gases is sought.

BACKGROUND OF THE INVENTION

There currently exists a number of methods and systems for the selective separation of gaseous feed streams, including, for instance, the removal of olefins from gas streams containing olefin and paraffin components. Transition metals such as copper, cobalt, nickel, manganese and silver have long been known to coordinate with unsaturated chemical species. This chemistry has been used extensively in synthesis, catalysis and analysis.

The utility of liquid membranes exploiting this coordination chemistry as a functional means of separating gases from one another is also known in the art. For instance, U.S. Pat. Nos. 3,758,603 and 3,758,605 describe the use of aqueous liquid membranes containing silver nitrate and supported on a variety of porous polymeric supports for the separation of olefins such as ethylene and propylene from paraffins such as methane and ethane.

Different liquid membrane systems have been used to accomplish other types of separations. For instance, it is known to use a cation-exchange membrane containing protonated ethylenediamine cations to separate $CO_2$ from various gas streams. This has again, however, entailed the use of an aqueous-based liquid membrane. There are inherent problems with the known, aqueous liquid membrane separation systems. One is that the constant exposure of the membrane to flowing gas streams necessitates the humidification of the streams to prevent the membrane from drying out, thereby destroying its utility. Another is that an aqueous system limits the range of facilitators capable of being used to those that are water soluble. Still another is that membrane support materials, such as polysulfone, are often hydrophobic, and are difficult to wet and even more difficult to maintain wetted. Drying out of the polymer support results in open channels that allow the permeation of the unseparated feed gas stream, at best resulting in severe drops in permeate purity.

Due to the inherent problems with aqueous membrane systems, an organic liquid membrane might be considered as advantageous. Nevertheless, not all organic solvents can be used for membrane based gas separations. Organic solvents such as ethylene glycol, glycerol and DMSO have proven to be less than desirable, as all yield olefin permeabilities much lower than those of their aqueous counterparts.

Therefore, a need exists for a liquid membrane system employing a liquid component which is resistant to membrane dry-out and which will eliminate the need for humidified gas streams. The liquid component should have viscosities and dielectric constants comparable to those of water, in order to take advantage of current support component technology.

SUMMARY OF THE INVENTION

It is therefore, an object of the present invention, to provide a facilitated liquid membrane useful in the selective separation of olefins from a gas feed stream.

It is another object of the present invention to provide a facilitated liquid membrane as above, which exhibits a decreased tendency to drying out due to exposure to the flowing gas feed stream.

It is a further object of the present invention, to provide a process for selectively separating olefins from a gas feed stream.

It is still another object of the present invention, to provide a process as above, which will be capable of providing increased permeate quantity and purity.

These and other objects, together with the advantages thereof over known liquid membranes, which shall become apparent from the following specification, are accomplished by the invention hereinafter described and claimed.

In general, a facilitated liquid membrane for the separation of olefins from a gaseous feed stream comprises a porous support membrane and a liquid membrane which comprises an aqueous solution containing a metal salt facilitator capable of coordination with olefin gases, and an alkyl carbonate co-solvent.

A process according to the present invention for the separation of olefins from a gaseous feed stream comprises the steps of passing a gaseous feed stream over one side of a facilitated liquid membrane and then collecting the olefins on the other side of the membrane system. The facilitated liquid membrane comprises a porous support membrane and a liquid membrane. The liquid membrane in turn comprises an aqueous solution containing a metal salt facilitator capable of coordinating with olefin gases, and an alkyl carbonate co-solvent.

PREFERRED EMBODIMENT FOR CARRYING OUT THE INVENTION

The present invention relates to selective separation of olefins from a gas feed stream. Exemplary of the possible separations according to the invention are those involving an olefin/paraffin gas stream, such as encountered in refinery off-gases, olefin/paraffin upgrading, gas purification and the like.

The facilitated liquid membrane according to the present invention comprises two components. The first is a porous support member which carries the second component, which is a liquid membrane.

The support member is preferably, a micro-porous polymer. The composition of the support member is not critical inasmuch as the member basically acts as an inert support for the liquid membrane. The support member should be inert to the potentially harsh solvating power of the carrier species, which is often of a high salt concentration; it may be isotropic or anisotropic; and, it may further be hydrophobic or hydrophilic. Suggested support materials include polysulfone, cellulose acetate, regenerated cellulose, polyamide, polycarbonates, polyimides, and fine pore ceramics, metals or glasses, among others. Polysulfone hollow fibers are preferred because they have high porosity and strength.

The membrane of choice should have a molecular weight cut off (MWCO) of from 500 (10 Å) to about 100,000 (200 Å), preferably from about 2,000 to about 20,000. These membranes have pore size ratings similar to typical ultrafiltration membranes. Membranes useful for the present invention include those membranes which are strong enough to withstand the operating pressures without bursting or collapsing, or without having the facilitator solution forced out of the membrane pores.

The membranes suggested for use herein may be skinned (anisotropic) membranes. For such membranes, the skin is usually about 500 Å to about 10 microns thick. This thin layer is the initial separating layer and is responsible for the pressure integrity of the membrane. It has a characteristic pore size, which determines the amount of pressure under which the membrane will remain efficiently functional.

Figure 1:
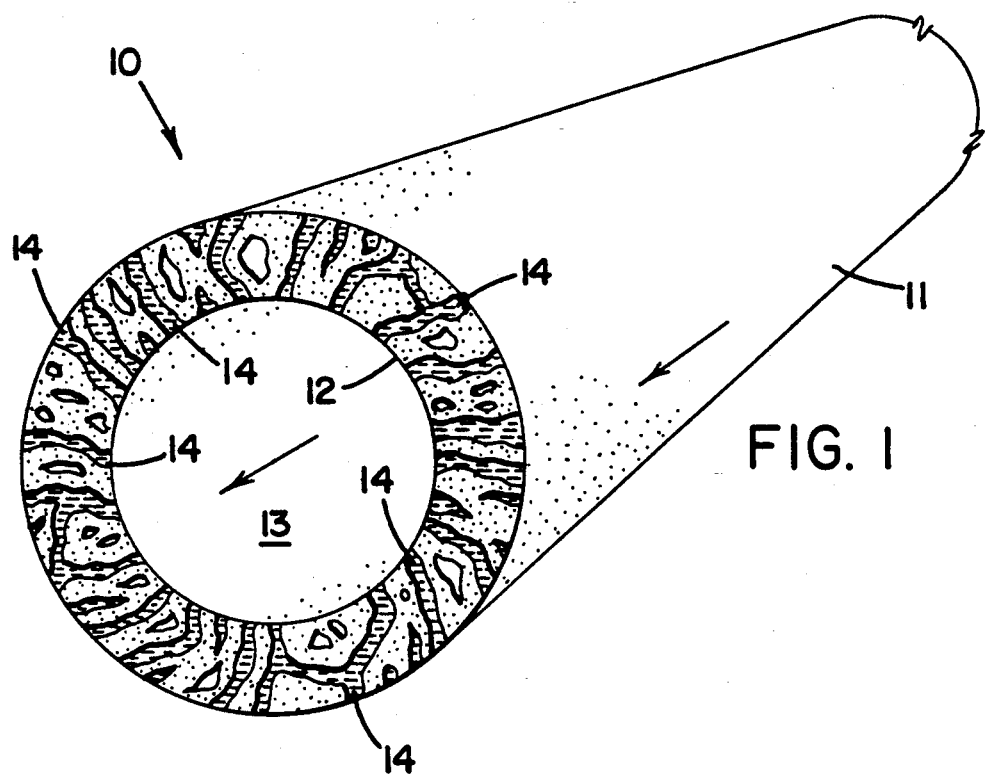
FIG. 1 is a cross-sectional, end view of a hollow fiber support member useful for the practice of the present invention.

FIG. 1 depicts a hollow fiber 10, useful as a support member in the present invention. Hollow fiber 10 has an outer wall 11 and an inner wall 12. Inner wall 12 defines a bore 13. Between walls 11 and 12 are a plurality of usually irregular pores 14. Pores 14 allow communication or an open passageway from outer wall 11, through inner wall 12 and into bore 13.

Figure 2:
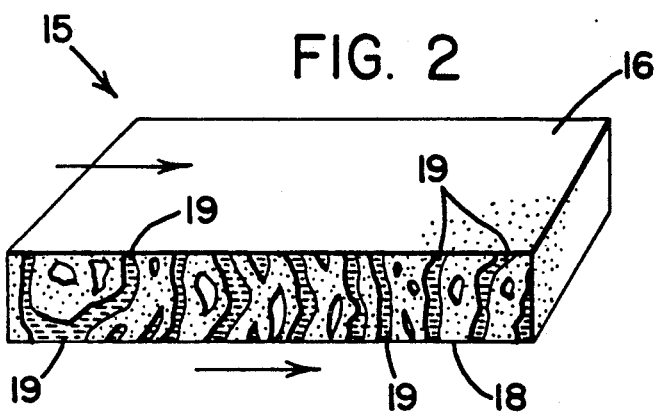
FIG. 2 is an enlarged perspective view of a flat sheet support member useful for practice of the present invention.

In addition to hollow fibers, other useful configurations for the support component include those fashioned from flat sheets of the support component material, as well as tubular configurations and spiral wound modules from flat sheets. A typical flat sheet support member 15 is depicted in FIG. 2. It has an upper, or first flat surface 16 and a lower, or second flat surface 18 and a plurality of irregular pores 19 therebetween.

The support member is charged with the liquid membrane such that it is saturated, i.e., the pores of the support member are loaded with the liquid membrane. Actual separation occurs when the gas phase component to be separated dissolves in the membrane at the feed gas/membrane interface. The dissolved gas, which is normally the olefin in an olefin/paraffin gas separation, diffuses or is carried via a variety of mechanisms to the product side of the membrane system, where it is collected, such as by employing a sweep gas stream.

The liquid membrane consists of an aqueous solution containing water and an alkyl carbonate as co-solvents and a facilitator. The facilitator employed is one which will reversibly complex with the olefin to be removed from the feed stream. Usually a metal complex is employed, however, other materials with favorable coupling/decoupling kinetics and acceptable solubilities in the liquid media may also be used. Among the known useful facilitators for olefin separation are the salts of the metals Ag, Cu, Mn, Zn, Pt, Pd, Ni, Co, Fe, Ru, Rh, Cr and Mb known to complex with olefins. Particularly useful are the silver salts $AgF$, $AgNO_3$, $AgClO_4$ and $AgBF_4$.

The membrane facilitated liquid, comprising the support member and the liquid membrane, is subjected to the flow of the feed gas stream, and perhaps a sweep stream on the product side of the membrane system. As noted hereinabove, this has been found to cause the liquid membrane to dry out resulting in open support member pores, increased permeation of the unseparated gas feed stream and decreased permeate purity. It has been found that membranes using water alone as a solvent are particularly prone to drying out, because of the relatively low boiling point of water.

Accordingly, the solvent of the liquid membrane system is preferably an alkyl carbonate providing two alkyl groups, joined together to form a cyclic structure or separate, each group having from 1 to about 5 carbon atoms, with ethylene carbonate and propylene carbonate being preferred. These alkyl carbonates represent a group of organic liquids having a boiling point in excess of 220° C. Thus, they may be exposed to the gas feed streams for extended periods of time before they begin to dry out. For example, in the experimental work presented hereinbelow, a membrane according to the present invention was successfully employed for a period of about 48 hours before performance was affected. Of course, greater periods of time may be obtained and thus, it is to be appreciated that the present invention is not limited to facilitated liquid membranes that last for a specific period of time but that in general, the membranes will last considerably longer than membranes using water alone as the solvent. Additionally, increasing the time before drying out occurs, also improves the permeate purity, and improves the longevity of the membrane system.

Water is also employed as a co-solvent. A co-solvent mixture is prepared and has from about 1 to about 99 percent by weight of the alkyl carbonate co-solvent, and from about 99 to about 1 percent by weight of water. The metal salt facilitator is placed into solution within the co-solvent mixture, such that the solution has a normality (N) of from about 0.1 to about 10, with a preferred range of from about 1 to about 5.

It has been found that hydrophobic support members, such as those made of polysulfone, are often incompatible with aqueous facilitator solutions. The present invention minimizes this effect by making the membrane system more hydrophilic or by making the liquid membrane solution more organic in nature. The alkyl carbonates of the present invention are particularly suited to accomplishing this object. As is generally known, the hydrophobic support can be first saturated in methanol and then water to "wet" the pores, which steps can be employed prior to saturating the support member with the liquid membrane solution of the present invention.

Sufficient membrane solution is employed for complete saturation of the pores of the support member, as depicted by stipling in FIGS. 1 and 2. Saturation of the support member pores is dependent upon the time employed to achieve saturation and the amount of agitation or the like employed, and is generally not dependent upon the amount of membrane solution present. An excess volume of membrane solution is used during saturation procedures.

The process according to the present invention is directed toward selective separation of olefins from a gas feed stream. In particular, the present process invention involves separating gas feed components by exposing a facilitated liquid membrane to the feed stream. The present invention is particularly suited to separation of olefins from gas streams.

A facilitated liquid membrane is prepared according to the present invention as described above, and employs a support member preferably comprising a microporous polymer as also described hereinabove, which is saturated with an excess of the liquid membrane solution. The support member pore saturation step may be accomplished by a variety of mechanisms. For instance, the support member may be simply soaked in the membrane solution for a number of hours. Agitation may be employed to expedite the saturation step. The actual saturation mechanism is not critical to the present invention. It is only necessary that complete loading of the support member pores be obtained, because open pores allows feed stream permeation.

A gas feed stream is caused to contact one side of the membrane system. At the interface between the feed stream and the membrane, the desired olefin is dissolved in the membrane solvent, and is caused to migrate to the opposite, product side of the membrane via a variety of mechanisms. At the product side of the membrane, the permeate may be collected, such as by the use of a sweep gas stream.

Exposure of the facilitated liquid membrane to the feed gas stream may take place for as long as the feed stream contains non-separated components. Furthermore, the exposure may take place for as long as the membrane system integrity remains. Once the solvent begins to dry out, and the support component pores begin to open, the process may be terminated, or the membrane system may be regenerated and returned to use. Regeneration merely requires a repeat of the liquid membrane saturation step for several hours or until the pores of the porous support are again saturated.

GENERAL EXPERIMENTAL

In order to demonstrate practice and the effectiveness of the present invention, a number of olefin/paraffin gas separations were conducted. Separations were conducted with flat sheet support components and with hollow fibers.

For the first series of separations, a flat sheet membrane was obtained from a commercial source. The sheet, Spectrum/Spectra por, is of a natural cellulose material which has a molecular weight cut-off of from about 6000 to about 8000, and which is about 3.1 mil thick.

A 6.0 cm disc was cut from the sheet and soaked with agitation in methanol for a minimum of 10 hours. The disc was then soaked in water with agitation for an additional 10 hours. A 3.0N $AgBF_4$ solution was prepared in a propylene carbonate/water (50/50) mixture. The washed disc was soaked in this solution with agitation for a minimum of 10 hours. The disc then supported a 3.0N $AgBF_4$ facilitated liquid membrane in propylene carbonate and water (50/50).

Figure 3:
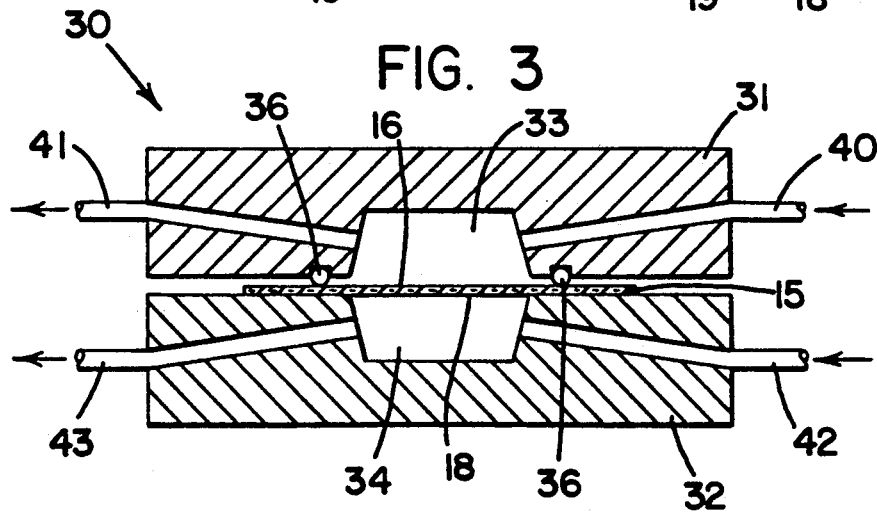
FIG. 3 is a cross-section of a flat sheet support member, as depicted in FIG. 2, in use in a testing cell.

The liquid membrane and flat sheet support member were then placed in a testing cell 30 as shown in FIG. 3. The testing cell consisted of a first and second body portion 31 and 32, respectively, each having a chamber 33 and 34, respectively. The flat sheet support member and liquid membrane 15 was suspended between chambers 33 and 34, and an O-ring seal 36 was employed to seal both sides of the membrane.

A test gas, as described below, was fed over one side 16 of the flat sheet support member and liquid membrane 15 via gas input conduit 40 and exit conduit 41 of the first body section 31. The test gas mixture comprised 14 percent ethylene, 14 percent ethane and 72 percent helium and was fed through cavity 33 at about 25° C. and at a flow rate of about 50 cc/min.

Similarly, a sweep gas was fed over the other side 18 of the membrane by introduction via gas input conduit 42 and exited via exit conduit 43, of the second body section 32. The sweep gas passed through cavity 34 was helium, fed at a flow rate of 20 cc/min. The permeate (sweep stream) was analyzed for ethylene and ethane. After 3 hours of run time permeate analysis showed an ethylene permeability of $2.0 \times 10^{-7}$ cc·cm/cm²·sec·cmHg and an ethane permeability of $3.0 \times 10^{-10}$ cc·cm/cm²·sec·cmHg.

For comparison, a similar facilitated liquid membrane was studied employing a 100 percent aqueous membrane. This system yielded an ethylene permeability of $1.7 \times 10^{-7}$ cc·cm/cm²·sec·cmHg and an ethane permeability of $3.4 \times 10^{-10}$ cc·cm/cm²·sec·cmHg.

Further tests were conducted using an ALPHA-10 flat sheet polysulfone support member. ALPHA-10 is a slightly hydrophobic polysulfone sheet produced by Filtron. Discs of 5.0 cm diameter were cut from the sheets and soaked in methanol with agitation for a minimum of 15 hours to thoroughly wet the member. The discs were then soaked in water with agitation for a minimum of an additional 15 hours. Each individual disc was then removed and placed in a solution of the particular medium that was to be investigated as a liquid membrane. The experiments performed on these membranes were run in pairs using both cells of a dual-cell system. One cell employed a membrane soaked with a 100 percent aqueous 4.0N $AgNO_3$ solution and the other membrane was soaked with a water/ethylene carbonate (80 percent by weight and 20 percent by weight, respectively) 4.0N $AgNO_3$ solution.

Figure 4:
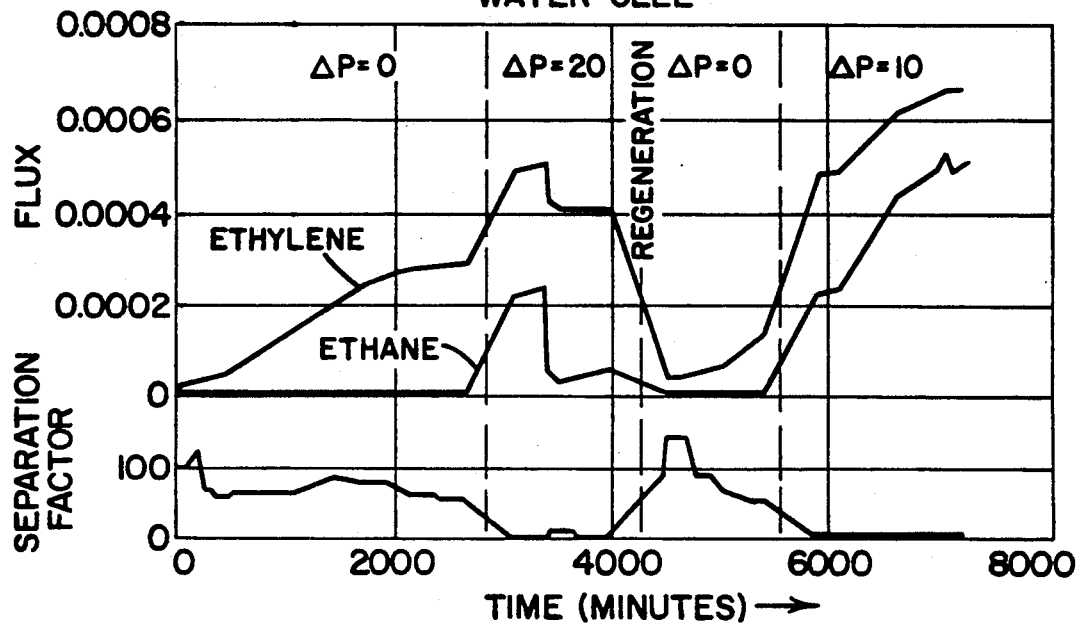
FIG. 4 is a graphical representation of test results obtained from an ethylene/ethane feed stream separation using a flat sheet polysulfone support member carrying water as a solvent for the metal salt facilitator.
Figure 5:
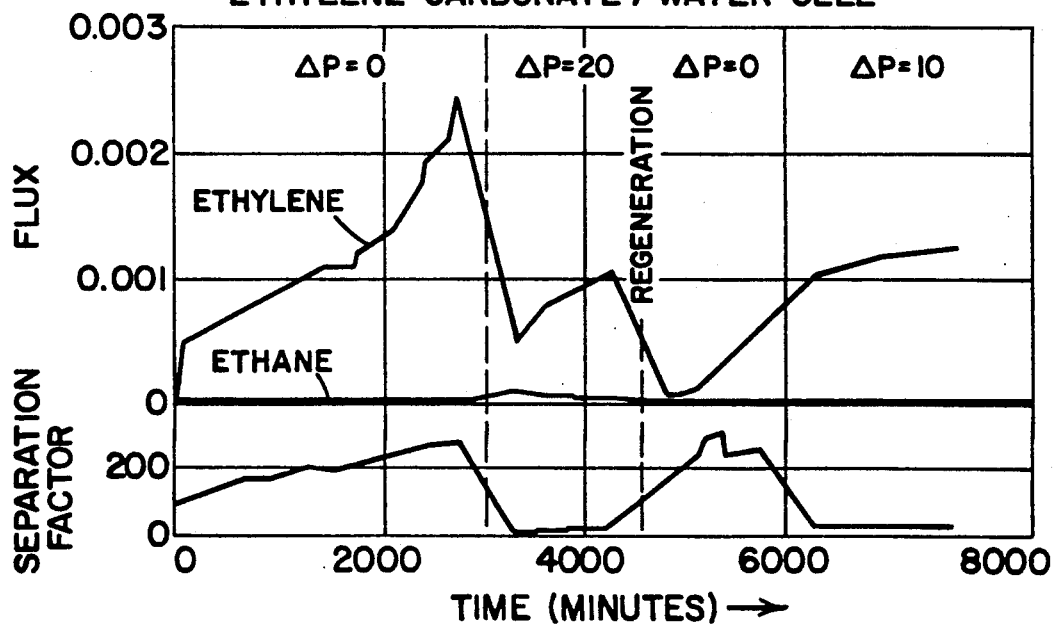
FIG. 5 is a graphical representation of test results obtained from an ethylene/ethane feed stream separation using a flat sheet polysulfone support member carrying ethylene carbonate and water as co-solvents for the metal salt facilitator.

Experiments were carried out using a 14 percent ethylene, 14 percent ethane, 72 percent helium test gas. When run with no pressure differential across the membrane, both the water and water/ethylene carbonate membranes retained some integrity, yielding fluxes in the range of 1.0–3.0×10$^{-4}$ cc/cm$^2$·sec and 1.0–3.0×10$^{-3}$ cc/cm$^2$·sec respectively. While both cells showed steadily increasing olefin permeation, the water cell also displayed an increasing ethane flux. The water/ethylene carbonate cell showed a constant ethane flux. As a result, the separation factor of the water cell settled around 60 while that of the water/ethylene carbonate cell gradually climbed from 100 to about 280. The results of the flat sheet polysulfone and 100 percent water membrane are represented graphically in FIG. 4, and the results of the same membrane with a water/ethylene carbonate 4.0N AgNO$_3$ solution are represented in FIG. 5.

The increasing ethane flux observed for the water cell indicated that thinning of the liquid membrane was probably occurring, i.e. water was leaving the hydrophobic polymer support member. The presence of 20 percent ethylene carbonate greatly reduced the incompatibility between the solution and the polymer support, resulting in less drying and a constant ethane flux during the first 40 hours of experiment for the water/ethylene carbonate cell. When the test gas pressure was raised to produce a pressure differential across the membrane of 20 psi (0.138 MPa), both cells failed, having a separation factor of less than 10.

The membranes were then regenerated with their respective solutions and tested once more, beginning with no pressure differential across the membrane. The results were comparable to the previous 0 psi runs. When the pressure differential across the membrane was raised to 10 psi (0.069 MPa), the water cell failed immediately. Fluxes of both ethylene and ethane increased dramatically for the water cell and the observed separation factor was less than 2. The water/ethylene carbonate cell still yielded an acceptable performance, with an ethylene flux of 1.2×10$^{-3}$ cc/cm$^2$·sec and a separation factor of about 50.

The addition of the alkyl carbonate to the AgNO$_3$ solution did reduce the incompatibility between the solution and the flat sheet polymer support member and increased the longevity of the membrane system.

Figure 6:
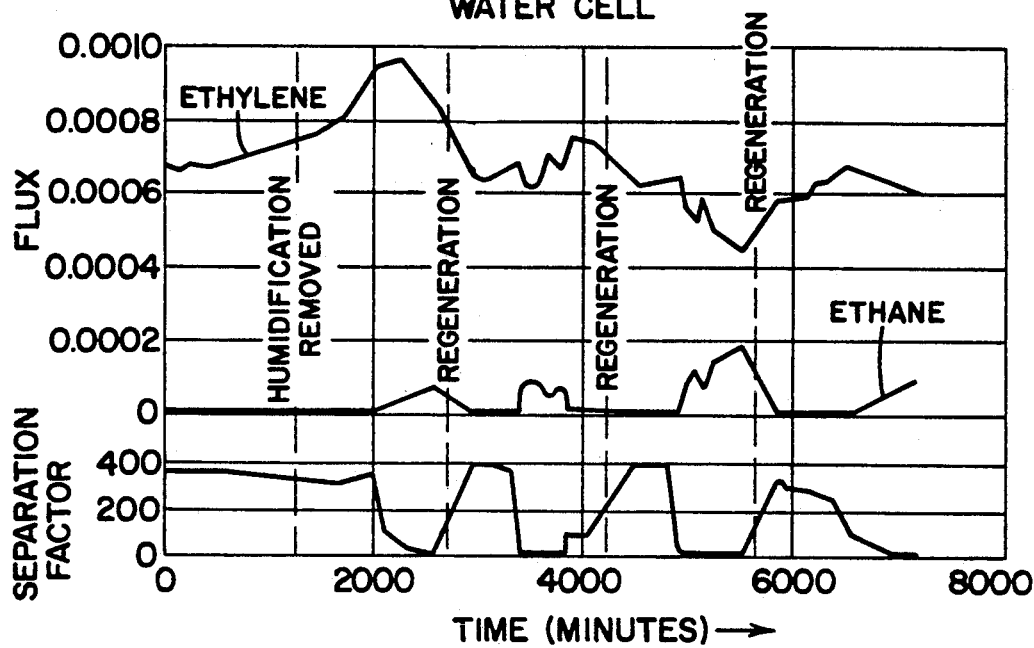
FIG. 6 is a graphical representation of test results obtained from an ethylene/ethane feed stream separation using a hollow fiber polysulfone support member carrying water as a solvent for the metal salt facilitator.
Figure 7:
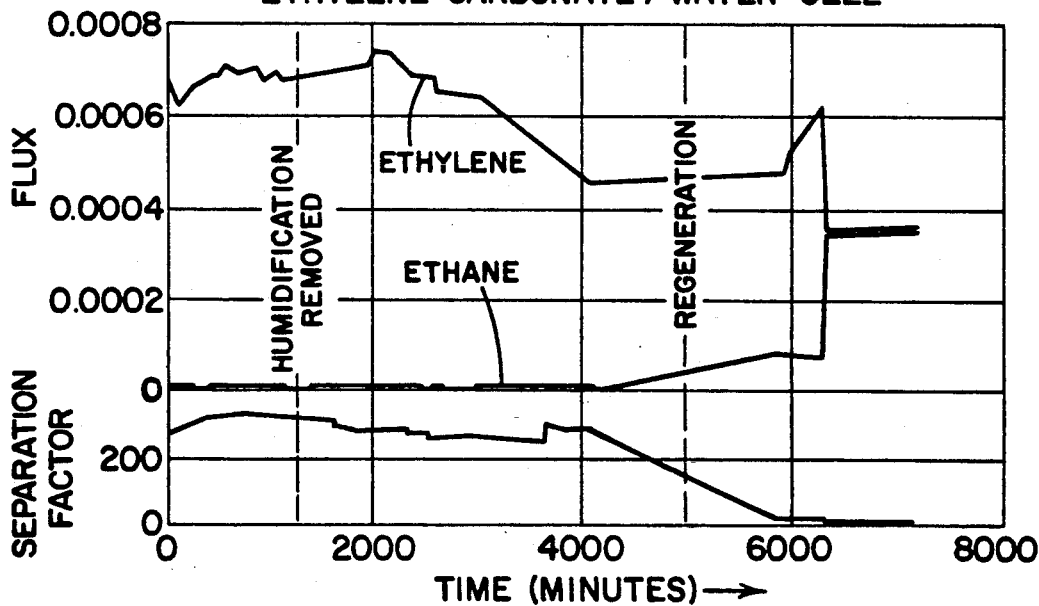
FIG. 7 is a graphical representation of test results obtained from an ethylene/ethane feed stream separation using a hollow fiber polysulfone support member carrying ethylene carbonate and water as co-solvents for the metal salt facilitator.

Another series of separations were conducted using polysulfone hollow fibers 10 as the support member. A casing was prepared out of stainless steel tubing and end fittings. The necessary number of fibers to yield the desired surface area were drawn through the casing and potted at the ends with epoxy. After the epoxy was set, the module was evacuated with a vacuum and flushed with 400 ml of distilled water. Excess water was blown out and the module was then flushed with 100 ml of the membrane solution to be tested. The excess solution was again blown out and the module was connected to the testing system. Again the experiments were run in pairs with one cell containing a pure aqueous 3.0N AgNO$_3$ solution and the other containing a water/ethylene carbonate (80/20) AgNO$_3$ solution. All experiments were carried out at room temperature using a 14 percent ethane, 14 percent ethylene, 72 percent helium test gas and a 100 psi (0.689 MPa) pressure differential across the membrane (100 psig test gas). These results are shown graphically in FIGS. 6 and 7.

The modules were run with the sweep gas humidified to determine initial stability. Both modules yielded ethylene fluxes of about 7.0×10$^{-4}$ cc/cm$^2$·sec with separation factors of about 300 and 250 respectively. After about twenty-four hours the humidification was removed from both modules.

Several hours after the removal of humidification, the water module began to show signs of drying out. The first sign of drying out was a steady increase in both ethylene and ethane flux due to the liquid membrane becoming thinner. Ten hours after the removal of humidification the water module failed with a rapid increase of ethane flux and a large decrease in separation factor. The water module was regenerated by flushing with an aqueous 3.0N AgNO$_3$ solution for 90 minutes and then put back on-stream. The regeneration returned the module to its original state of performance. However, the regenerated module lasted only about seven hours. The module failed again and a second regeneration was required. The regeneration again returned the module to more or less its original state of performance. The module after the second regeneration lasted only about five hours. A third regeneration was then performed which returned the failed water module to its original state for about eight hours. Because these experiments were carried out with an unhumidified helium sweep gas (10 cc/min), they can be considered as accelerated drying tests for this polysulfone module. Under these accelerated drying conditions, the module with the aqueous AgNO$_3$ solution failed in less than 10 hours each time and each time a simple regeneration successfully brought the module back to its original state.

By contrast, the module containing 20 percent ethylene carbonate ran for almost 48 hours after the removal of the humidification before its performance indicated that module dry-out was becoming a problem. The drying out for the water/ethylene carbonate module was indicated by a slow and gradual drop in both ethylene and ethane flux. The presence of the organic component in the solvent mixture again improved the incompatibility between the solution and the polymer support and increased the longevity of the hollow fiber membrane module.

Figure 8:
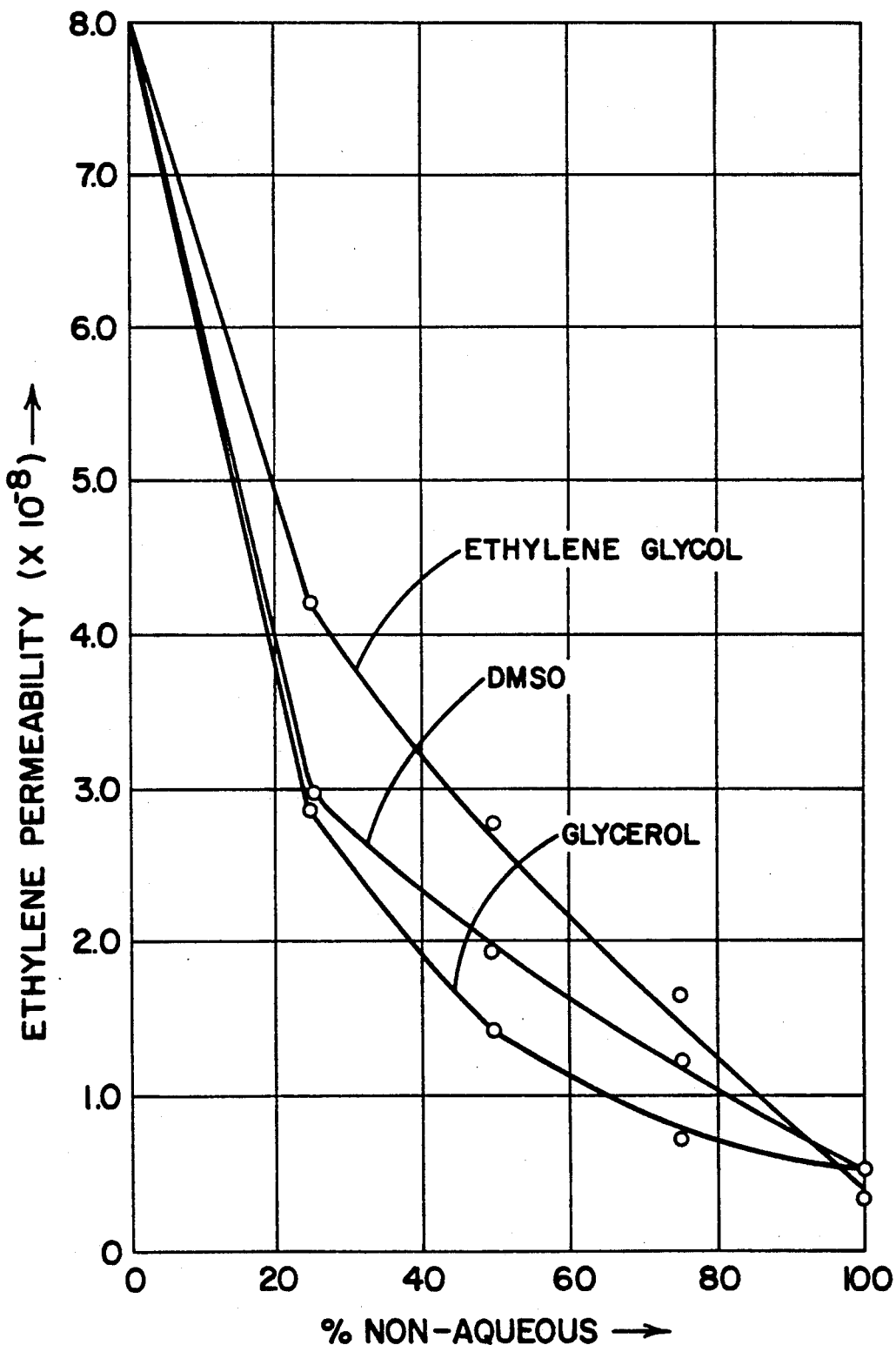
FIG. 8 is a graphical representation of test results obtained from an ethylene/ethane feed stream separation using a flat sheet cellulose material as the support member and carrying a non-ethylene carbonate and water as co-solvents for the metal salt facilitator; and, FIG. 9 is a graphical representation of test results obtained from an ethylene/ethane feed stream separation using a flat sheet cellulose material as the support member and carrying propylene carbonate and water as co-solvents for the metal salt facilitator, compared with ethylene glycol and water as co-solvents for the metal salt facilitator.

Based upon the improved results attendant the use of ethylene carbonate, several other organic solvents were selected and evaluated with water to organic solvent ratios of 100:0, 75:25, 50:50, 25:75 and 0:100. The solvents ethylene glycol, glycerol and dimethyl sulfoxide (DMSO) were employed with 2.0N AgNO$_3$ in a Spectra por membrane and were run in cells using the test gas described hereinabove and the same conditions. The ethylene permeability as a function of solvent composition has been plotted in FIG. 8. In FIG. 9, the organic solvents propylene carbonate and glycerol were compared again at varying concentrations with water, and utilizing a Spectra por membrane, run in cells using the same test gas and conditions described hereinabove.

As is evident from the graphs, the greatest ethylene permeability occurred utilizing 100 percent water as the solvent. A dramatic drop in permeability resulted with the addition of only 25 percent organic solvent for all three examples in FIG. 8 and glycerol for FIG. 9. Permeability continued to decrease, although at a lesser rate, with increasing concentrations of the organic solvents. Use of propylene carbonate, however, did not result in a decrease in permeability until the 100 percent levels. Actually perfomance can be expected to decrease somewhere in the range of more than 75 percent propylene carbonate although no such example was run.

In conclusion, the hydrophobicity of the polysulfone membrane material has a profound effect on the performance of the aqueous AgNO$_3$ solution facilitated olefin transport. The addition of a high-boiling organic component in the solvent can and does decrease the drying-out problem and increase the lifetime of the olefin/paraffin separation system.

It should be clear from the foregoing examples and specification disclosure, that facilitated liquid membranes for olefin separations according to the present invention, exhibit improved permeate purity, due to a decrease in the drying out of the liquid membrane during separation procedures.

It will be understood by those skilled in the art, that while the present invention has particular application to the separation of olefins, it has equal applicability to the separation of other components as well. While the silver salts disclosed herein complex with olefins, it is to be understood that such salts may complex with other chemical species, enabling these species to be separated by the process of the invention. Furthermore, other facilitators may be employed which would prove useful as a complexing agent in a separation operation as described hereinabove, making all such facilitators encompassed by the spirit of the present invention. In similar fashion, it is to be understood by those skilled in the art that the present invention can be practiced with water and alkyl carbonate cosolvents other than those described herein. Thus, those skilled in the art can readily select a facilitator as well as a co-solvent according to the disclosure made herein.

Finally, it is to be understood that the present invention can be practiced with other support materials, metal salt facilitators and alkyl carbonate co-solvents than those exemplified herein, the examples having been provided merely to demonstrate practice of the subject invention. And thus, it is believed that any of the variables disclosed herein can be readily determined and controlled without departing from the scope of the invention disclosed and described. Moreover, the scope of the invention shall include all modifications and variations that fall within the scope of the attached claims.

We claim:

1. A process for the separation of olefins from a gaseous feed stream comprising the steps of:
    passing a gaseous feed stream over one side of a facilitated liquid membrane which comprises
    a porous hydrophobic support member having a first surface and a second surface;
    said first surface and said second surface being integrally formed with and consisting of the same material as said porous support member; and
    a liquid membrane, said liquid membrane comprising
    an aqueous solution containing a metal salt facilitator capable of coordinating with olefin gases; and
    an alkyl carbonate co-solvent; and
    improving the compatibility between said porous support member and said liquid membrane by having included said alkyl carbonate co-solvent in said liquid membrane.

2. A process, as set forth in claim 1, further comprising the steps of monitoring the purity of said collected olefins and regenerating the membrane when said collected olefins are found to contain appreciable quantities of the other gases of the gas feed stream.

3. A process, as set forth in claim 1, comprising the further step of preparing the facilitated liquid membrane.

4. A process, as set forth in claim 3, including the further step of saturating said porous support member with said liquid membrane.

5. A process, as set forth in claim 4, wherein said alkyl carbonate co-solvent provides two alkyl groups, separate or joined together to form a cyclic structure and each having from 1 to about 5 carbon atoms.

6. A process, as set forth in claim 5, wherein said liquid membrane comprises from about 99 percent to about 1 percent by weight of water and from about 1 percent to about 99 percent by weight of said co-solvent.

7. A process, as set forth in claim 6, wherein said metal salt facilitator comprises a salt of a metal selected from the group consisting of Ag, Cu, Mn, Zn, Pt, Pd, Ni, Co, Fe, Ru, Rh, Cr and Mb known to complex with olefins.

8. A process, as set forth in claim 7, wherein said metal salt facilitator is selected from the group consisting of AgF, $AgNO_3$, $AgClO_4$ and $AgBF_4$.

9. A process, as set forth in claim 8, wherein said support member is polysulfone.

10. A process, as set forth in claim 9, wherein said co-solvent is selected from the group consisting of ethylene carbonate and propylene carbonate and said metal salt facilitator is $AgNO_3$.

11. A facilitated liquid membrane for the separation of olefins from a gaseous feed stream comprising:
    a porous hydrophobic support member having a first surface and a second surface;
    said first surface and said second surface being integrally formed with and consisting of the same material as said porous support member; and a liquid membrane, said liquid membrane comprising
    an aqueous solution containing a metal salt facilitator capable of coordinating with olefin gases; and
    an alkyl carbonate co-solvent;
    wherein said alkyl carbonate co-solvent improves the compatibility between said support member and said liquid membrane.

12. A facilitated liquid membrane, as set forth in claim 11, wherein said alkyl carbonate co-solvent provides two alkyl groups, separate or joined together to form a cyclic structure and each having from 1 to about 5 carbon atoms.

13. A facilitated liquid membrane, as set forth in claim 12, wherein said liquid membrane comprises from about 99 percent to about 1 percent by weight of water and from about 1 percent to about 99 percent by weight of said co-solvent.

14. A facilitated liquid membrane, as set forth in claim 13, wherein said metal salt facilitator comprises a salt of a metal selected from the group consisting of Ag, Cu, Mn, Zn, Pt, Pd, Ni, Co, Fe, Ru, Rh, Cr and Mb known to complex with olefins.

15. A facilitated liquid membrane, as set forth in claim 14, wherein said metal salt facilitator is selected from the group consisting of AgF, $AgNO_3$, $AgClO_4$ and $AgBF_4$.

16. A facilitated liquid membrane, as set forth in claim 15, wherein said support member is polysulfone.

17. A facilitated liquid membrane, as set forth in claim 16, wherein said co-solvent is selected from the group consisting of ethylene carbonate and propylene carbonate and said metal salt facilitator is $AgNO_3$.

18. A facilitated liquid membrane for the separation of olefins from a gaseous feed stream comprising:

a porous polysulfone support member having a first surface and a second surface;

said first surface and said second surface being integrally formed with and consisting of the same material as said porous support member; and a liquid membrane, said liquid membrane comprising an aqueous solution containing a metal salt facilitator capable of coordinating with olefin gases; and an alkyl carbonate co-solvent;

wherein said alkyl carbonate co-solvent improves the compatibility between said support member and said liquid membrane.

* * * * *